(12) United States Patent
Chou et al.

(10) Patent No.: US 7,871,378 B1
(45) Date of Patent: Jan. 18, 2011

(54) DEVICE AND METHOD TO MEASURE CORNEAL BIOMECHANICAL PROPERTIES AND ITS APPLICATION TO INTRAOCULAR PRESSURE MEASUREMENT

(75) Inventors: Jim-Son Chou, Irvine, CA (US); Steven Scott Heinold, Woodland Hills, CA (US); George Bryant Ismael, Rosamond, CA (US); Richard Arnold Moore, Canoga Park, CA (US)

(73) Assignee: Achevé Technology, Inc., Irvine, CA (US)

( * ) Notice: Subject to any disclaimer, the term of this patent is extended or adjusted under 35 U.S.C. 154(b) by 1373 days.

(21) Appl. No.: 11/305,551

(22) Filed: Dec. 16, 2005

Related U.S. Application Data

(60) Provisional application No. 60/639,059, filed on Dec. 22, 2004, provisional application No. 60/662,260, filed on Mar. 16, 2005, provisional application No. 60/665,271, filed on Mar. 25, 2005.

(51) Int. Cl.
*A61B 3/16* (2006.01)
(52) U.S. Cl. ...................................... 600/398; 600/401
(58) Field of Classification Search ................ 600/398, 600/401, 405
See application file for complete search history.

(56) References Cited

U.S. PATENT DOCUMENTS

| | | |
|---|---|---|
| 3,070,997 A | 1/1963 | Goldmann et al. |
| 3,585,849 A | 6/1971 | Grolman |
| 4,817,620 A * | 4/1989 | Katsuragi et al. ........... 600/401 |
| 5,474,066 A | 12/1995 | Grolman |
| 5,512,966 A | 4/1996 | Snook |
| 6,053,867 A | 4/2000 | Iijima |
| 6,113,542 A | 9/2000 | Hyman |
| 6,286,958 B1 | 9/2001 | Koest |
| 6,875,175 B2 | 4/2005 | Luce |
| 7,235,051 B2 * | 6/2007 | Iwanaga ..................... 600/401 |

OTHER PUBLICATIONS

Young, W.C.(1989) Roark's Formulas for Stress and Strain, McGraw-Hill, 6th Edn., pp. 523-546.

Orssengo G, Pye D, Determination of the true Intraocular Pressure and Modulus of Elasticity of the Human Cornea in vivo, Bulle. Of Mathematical Biology(1999) 61, 551-572.

Lu Wang, et.al Fast Fourier Transform analysis of dynamic data : stress-strain analysis of biological tissue, Phys. Med. Biol. (1997), 537-547.

(Continued)

*Primary Examiner*—Max Hindenburg
*Assistant Examiner*—Jonathan M Foreman

(57) ABSTRACT

This invention is a system, an apparatus and a method for measuring biomechanical properties of cornea and the intraocular pressure in vivo. More than one dimensional topographic information of the cornea is recorded and analyzed before and during the fluid discharge and converted to the stress-strain relationship and other cornea parameters, for example the cornea thickness and radius of curvature, etc. The deformation of cornea is initiated by a non-contact fluid discharge whose profile is predetermined and monitored in real time. Utilizing this non-contact topographer, the true intraocular pressure can be derived from the response of the cornea due to the impact of fluid discharge and the corneal topographic parameters. One embodiment of this invention includes the use of a multiple color strobe light/multiple detector system to record the corneal topographic deformation due to the impact of fluid discharge.

34 Claims, 4 Drawing Sheets

OTHER PUBLICATIONS

Liu, C. Roberts, Influence of corneal biomedical properties on intraocular pressure measurement, Quantitative Analysis, J cataract refract surg. 2005, 31, 146-155.

Anderson, A. El-Sheikh, T.Newson Application of structural Analysis to the mechanical behaviour of Cornea, J. R. Soc. Lond. Interface 2004 (1): pp. 1-13.

G. Grabner, R. Eilmsteiner, C Steindl, J, Ruckhofer, R. Mattioli, W. Husinsky, Dynamic corneal imaging, J cataract refract surg. 31, (2005), pp. 163-174.

D. Luce, Determining in vivo bio-mechanical properties of the cornea with an ocular analyzer, J cataract refract surg. 31, (2005), pp. 156-162.

* cited by examiner

DEVICE AND METHOD TO MEASURE CORNEAL BIOMECHANICAL PROPERTIES AND ITS APPLICATION TO INTRAOCULAR PRESSURE MEASUREMENT

CROSS-REFERENCE TO RELATED APPLICATIONS

This application claims the benefit of provisional patent applications with Ser. No. 60/639,059 filed 2004 Dec. 22, No. 60/662,260 filed 2005 Mar. 16 and 60/665,271 filed 2005 Mar. 25 by the present inventor.

FEDERALLY SPONSORED RESEARCH

Not Applicable

SEQUENCE LISTING OR PROGRAM

Not Applicable

BACKGROUND OF THE INVENTION

1. Field of the Invention

This invention relates generally to a device and method that measures the biomechanical properties, the stress-strain relationship of the cornea together with the physical properties of a mammal's anterior chamber of the eye in vivo. The present innovation also applies to methods to monitor the intraocular pressure of a mammal eye.

2. Prior Arts

Cornea contributes more than 60% of refractive power of the vision system thus most of the refractive surgeries for vision corrections were performed on the cornea. Current diagnostic instruments used in the eye clinics are able to measure the radius of curvature, the astigmatism and the thickness of cornea before, during and after the refractive surgeries. With all these measurement and the wave front technology, ultimate refractive surgical outcome was guaranteed. However the promises to enhance the predictability of surgical outcomes were not met, debilitating visual complaints are reported. Several studies indicate that bio-mechanical properties, the stiffness or the elasticity of the cornea plays a very important role of the stability of the cornea after refractive surgery.

The possibility of ectasia, the bulging of the cornea, after the ablation type of laser surgeries, for example LASIK, also demonstrates the unsatisfactory outcome of laser refractive surgeries due to the lack of biomechanical properties of corneas. Although the incident rate of ectasia appears low now, LASIK has only been used in clinical practice in recent years and the long-term results are unknown. Recent studies showed that the corneal thickness alone can not explain the ectasia incidents and bio-mechanical properties of the cornea are being suggested. Thus screening of the cornea for its biomechanical defects together with the cornea thickness radius of curvature and other physical parameters before LASIK type procedures is becoming more urgent.

Direct measurement of in vivo bio-mechanical properties in the human eye has been rare until recently. Grabner used video topographic method to measure the cornea distortion induced by an indenter which was powered by a micro-precision motor. This method requires contact of the patient's cornea with a pointed indenter and is not practical in the clinical setting. This device is not able to provide other physical parameters of the cornea. Luce measured the hysteresis of the cornea rebound due to the impact of an expanded air pulse to index the cornea biomechanical properties. Because it is based on the reflection of limited points of light, the method suffers from the same reliability problem when the surface of the cornea is irregular as the non-contact tonometer suffers. Furthermore, Luce's inventions, including U.S. Pat. No. 6,875,175, can not provide the physical parameters of the cornea, for example: radius of curvature and the thickness of the cornea, etc.

Another important clinical issue related to the lack of in vivo data of the cornea biomechanical properties has been demonstrated in the clinical monitoring of the intraocular pressure, an important indicator to control the progress of glaucoma. Current intraocular pressure measurement, no matter contact or non-contact tonometries, requires the measurement via the cornea. Both methods are based on the flattening of the cornea by external applanation forces and interpretation of the rebound force of cornea.

Maklakov was the first one who developed the impression tonometer in 1885. In this device, a plunger of a known weight is allowed to rest against the eye with the patient in a supine position. The area of contact is determined with a dye, and the weight divided by the area of contact gives the pressure.

The modern tonometer was invented in the 1950's by Goldmann (U.S. Pat. No. 3,070,997). In this device, a small biprism is pressed against the cornea. The cornea is prepared by applying a topical anesthetic and a dye which is illuminated by a slit lamp. The image of the glowing tear film around the edge of the prism is split by the biprism such that when just enough pressure is applied to applanate the cornea to the diameter of the prism, the half-images of the glowing ring become perfectly aligned. Great skill is required in order to obtain accurate measurements and the disturbances of the intraocular pulse must be averaged out visually. In general, tonometry measurements vary about 10% from examiner to examiner.

Grolman disclosed a non-contact tonometer, U.S. Pat. No. 3,585,849, which operates by impacting an air pulse at the cornea. The time for the cornea to return to the predetermined shape due to the impacting of the air pulse was measured via the optical reflection of a point light source upon the cornea and correlated to the intraocular pressure.

This non-contact device has several disadvantages: the reading is inaccurate on irregular cornea surfaces due to its single point probing system; it overestimates the tension with increased tear film and ocular misalignment and the reading is variable due to the ocular pulses in the eye. The device is of little clinical value above 30 mmHg due to lack of accuracy. In spite of the difficult clinical technique, possible damage to the cornea, chances of communicating disease and questionable accuracy, the contact tonometer, particularly the Goldmann tonometer, is the still gold standard of the measurement because of the problems with non-contact tonometers.

From the very beginning, both intraocular pressure measurements are known to vary as a function of corneal thickness, radius of curvature and rigidity and all of which may vary from patient to patient. Recently, more quantitative information of this interference is emerging clinically and theoretically.

The Ocular Hypertension Treatment Study (OHTS) reported the significant effect of Central Cornea Thickness (CCT) on intraocular measurement, CCT measurement was performed and used to correct the subsequent measurement by Goldmann applantation tonometer or non-contact tonometer with an empirical correlation formula. Grolman, U.S. Pat. No. 5,474,066, and Hyman, U.S. Pat. No. 6,113,542, proposed including the cornea thickness in the non-contact or contact tonometer measurement. In practice, variations were already reported using this approach, with non-contact tonometer measurement garnering the most variation.

This kind of variation was due to the fact that the thickness of the cornea alone does not account for the total resistance and effect of the cornea and thus the inaccuracy of the intraocular pressure.

These sources of inaccuracy of the tonometer measurement and the variability of corneas are accentuated in the more than 1 million patients per year who undergo corneal refractive surgery.

Recently, Orssengo and Roberts quantified the correlation between the cornea thickness, the curvature, the elasticity of the cornea and the intraocular pressure readings. Their finding together with some simulation calculation reemphasizes that the cornea factor needs to be isolated from any measuring method of intraocular pressure.

Thus, to improve the refractive surgeries and the intraocular pressure monitoring, there is a great national and international need to develop a comprehensive device to measure the biomechanical properties of the cornea.

OBJECTS AND ADVANTAGES

Accordingly, our invention of a non-contact ophthalmic device provides a new method for measuring the biomechanical properties of the cornea and the intraocular pressure by recording the sequence of multiple dimensional corneal profiles after the impact of a discharge of fluid. The biomechanical properties of the cornea derived from the corneal profiles will thus eliminate the cornea factor from the intraocular pressure measurement. Several objects and advantages of the present invention are:

(a) to provide the first in vivo and non contact measurements to obtain the biomechanical properties and other related corneal parameters, e.g. thickness and radius of curvature, etc.

(b) to provide a correlation between the topographic changes of the cornea and stress-strain relationship of the cornea.

(c) to provide an in vivo and non-contact way to screen patients for refractive surgeries in which no topical anesthetic is needed and there is a low risk of contamination (d) to provide a platform that can be used to monitor the cornea conditions after the refractive surgeries (e) to provide integral corneal biomechanical information to improve the predictability of the refractive surgeries (f) to provide an in vivo and non-contact way to obtain the true intraocular pressure.

SUMMARY OF THE INVENTION

In accordance with the present invention, an ophthalmic device comprises a fluid discharge system, a real time image recording/analysis system that records and analyzes the topographic changes of the cornea due to the impact of fluid discharge and an algorithm to convert topographic changes to the bio-mechanical properties of the cornea.

In one innovative aspect, the present innovation relates to dynamic corneal topographer and methods and sequences used within such systems. The topographic data can be recorded/reported on site of the measurement or via interne through a server and a web site and analyzed via numerical methods.

In another innovative aspect, the present innovation relates to use of high speed photography to record images of the event of cornea deformation during the impact of an external force.

In another innovative aspect, the present innovation relates to the use of short pulse to record the sequence in a recording media, particularly a multicolor short light sequence to record and display sequence of the cornea deformation in limited image frames during the impact of the external force.

In another innovative aspect, the present innovation relates to methods to monitor the glaucoma and the intracocular pressure of a mammal eye and more specifically to a non-contact type of intraocular pressure which uses corneal static and dynamic topographic measurement to eliminate the effect of cornea in the pressure measurement.

In another innovative aspect, the present innovation relates to an ophthalmic diagnostic system incorporating our invention for testing the integrity of the anterior chamber of a mammal eye and for methods of implementing and utilizing such a diagnostic systems.

BRIEF DESCRIPTION OF THE DRAWINGS

The nature and mode of operation of the present invention will now be more fully described in the following detailed description of the invention taken with the accompanying drawing figures, in which.

DETAILED DESCRIPTION

Figure 1A:
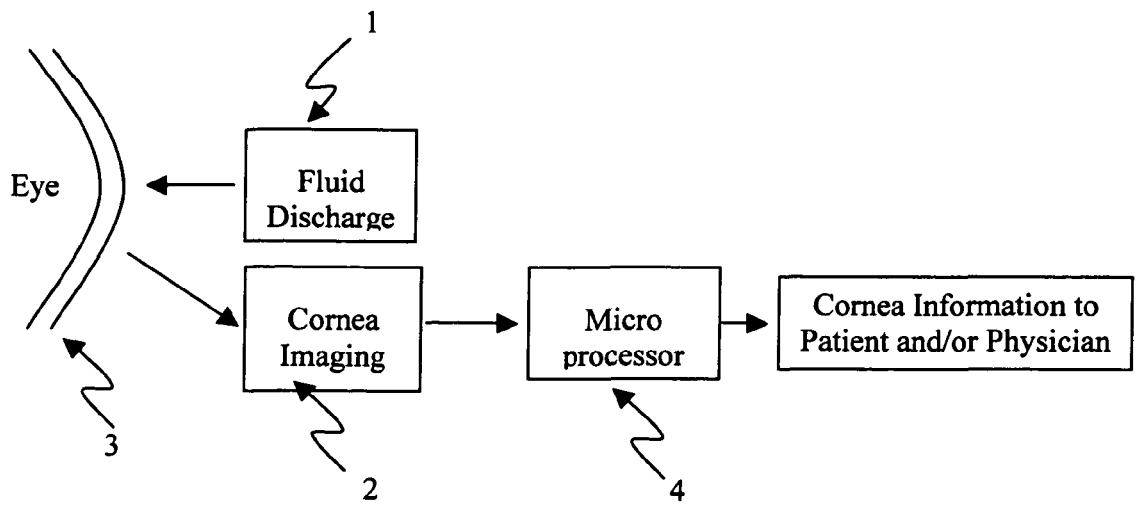
FIG. 1A and FIG. 1B are schematic block diagrams of the non-contact ophthalmic system to measure the biomechanical properties of the cornea.
Figure 1B:
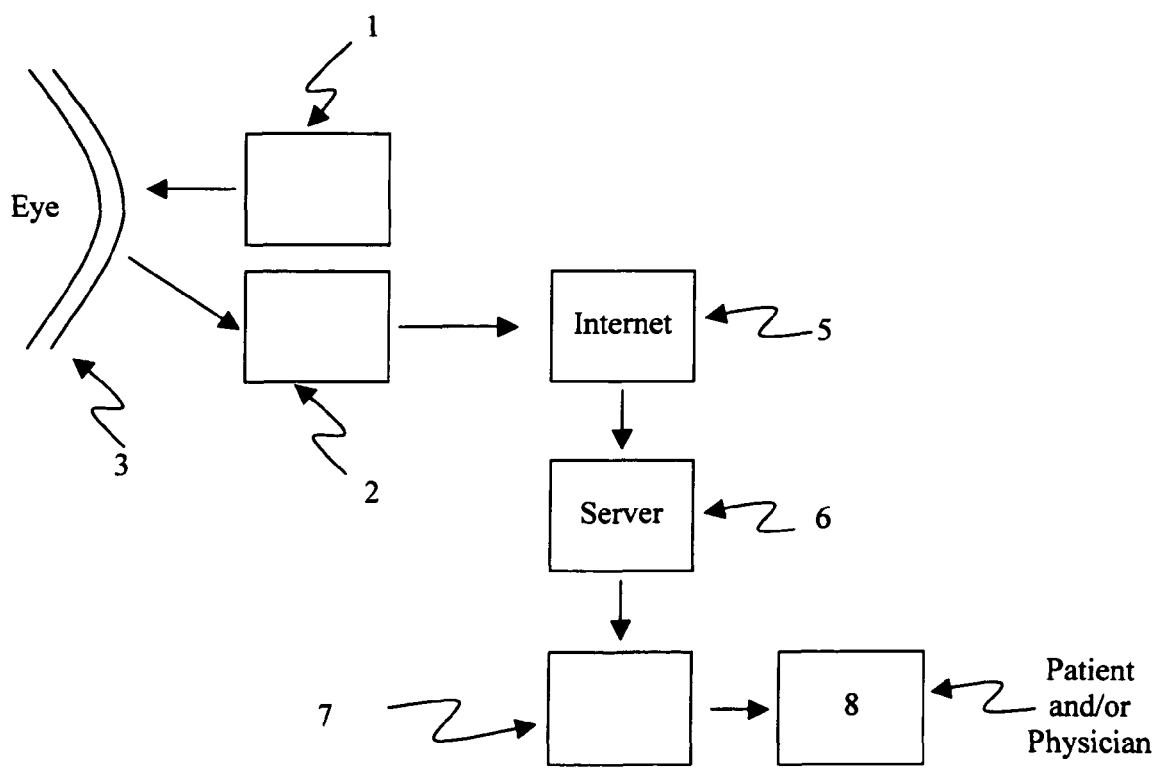

The system for use in the invention, as indicated in FIG. 1, has a fluid discharge device, 1, that discharges a pulse of the fluid with known stress profile and an image recording subsystem, 2, that records the profile of the cornea, 3, before, during and/or after the discharge of the fluid.

The cornea profiles obtained will then be used to derive the cornea parameters, e.g. the thickness, the radius of curvature, and biomechanical properties of cornea like stress-strain relationship etc., and calculate the intraocular pressure according the analytical formula and/or numerical simulations, e.g. finite element method, as describe in FIG. 1.

The fluid discharge device, 1, can be a generator that discharges air pulses. Our preferred embodiment is an enclosure with an orifice and a plunger, 18, of FIG. 2, driven by a solenoid or a linear motor, not shown in the drawing's. The plunger will drive the air through the orifice to create the impacting stress. The stress profile generated by the fluid discharge device can be predetermined and/or monitored during the discharge. This profile is to be used as the stress input and thus create a reliable and non contact input stress to initiate the cornea response as compared to the pointed indenter contacting with cornea suggested by Grabner's method.

The image recording subsystem, 2, is to obtain quantitative topographic information of the cornea presented in two or three spatial dimensions. With the multiple dimensional profiles, we are able to overcome some of the problems with using limited points to monitor the cornea responses due to the fluid discharge as suggested by Luce. Corneal topographic method for example, Jongsma, U.S. Pat. No. 5,406, 342, can resolve this problem by providing 2- or 3-dimensional topographic information, but such corneal topographic system comprises a light source and a receiving part that are closely coupled together and tend to be too complicated and intricate to be incorporated physically with the fluid discharging system., 2.

Figure 2:
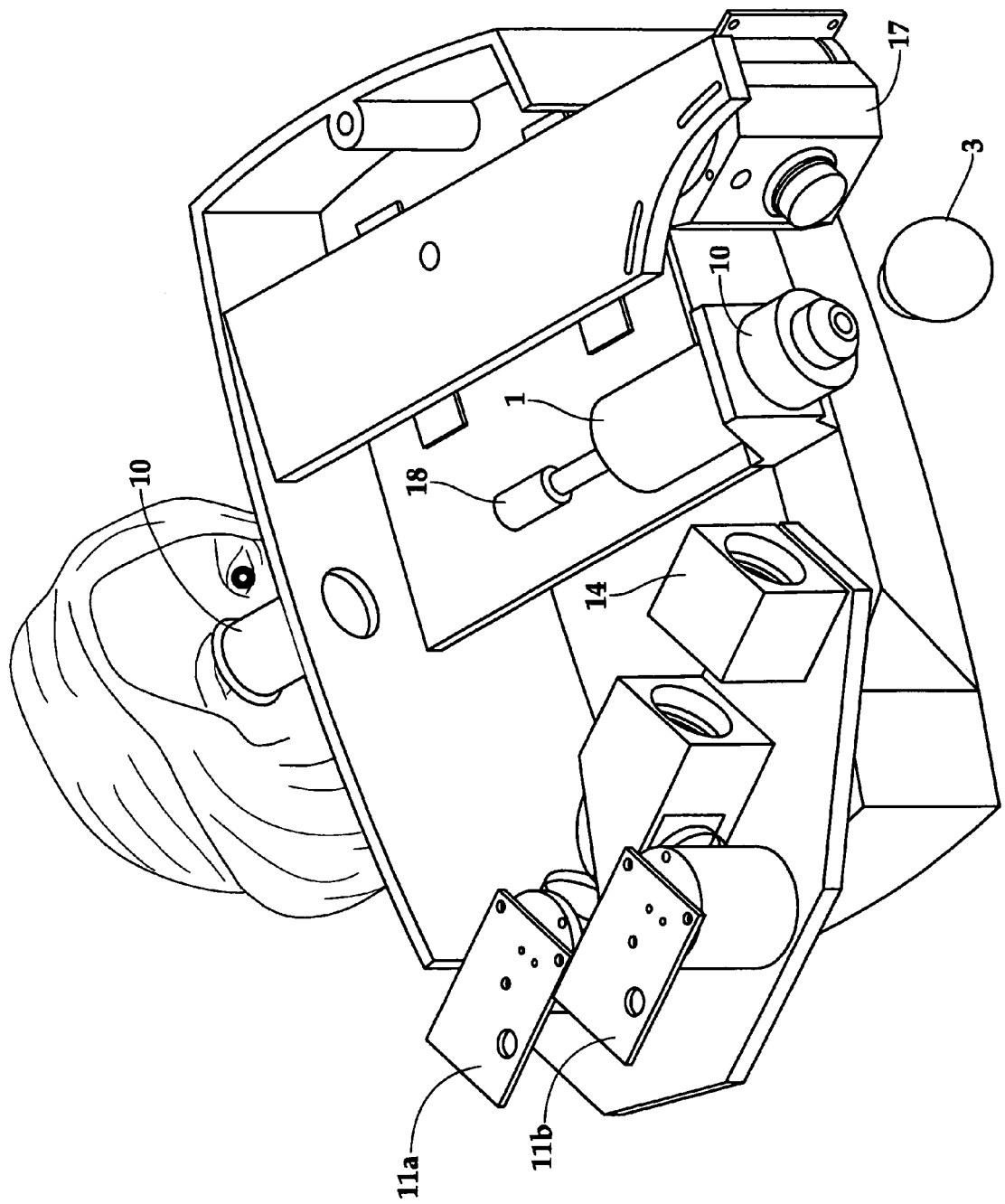
FIG. 2 is a perspective view of a high speed profile photography system embodying the present invention of a non-contact corneal biomechanical measurement system.
Figure 3:
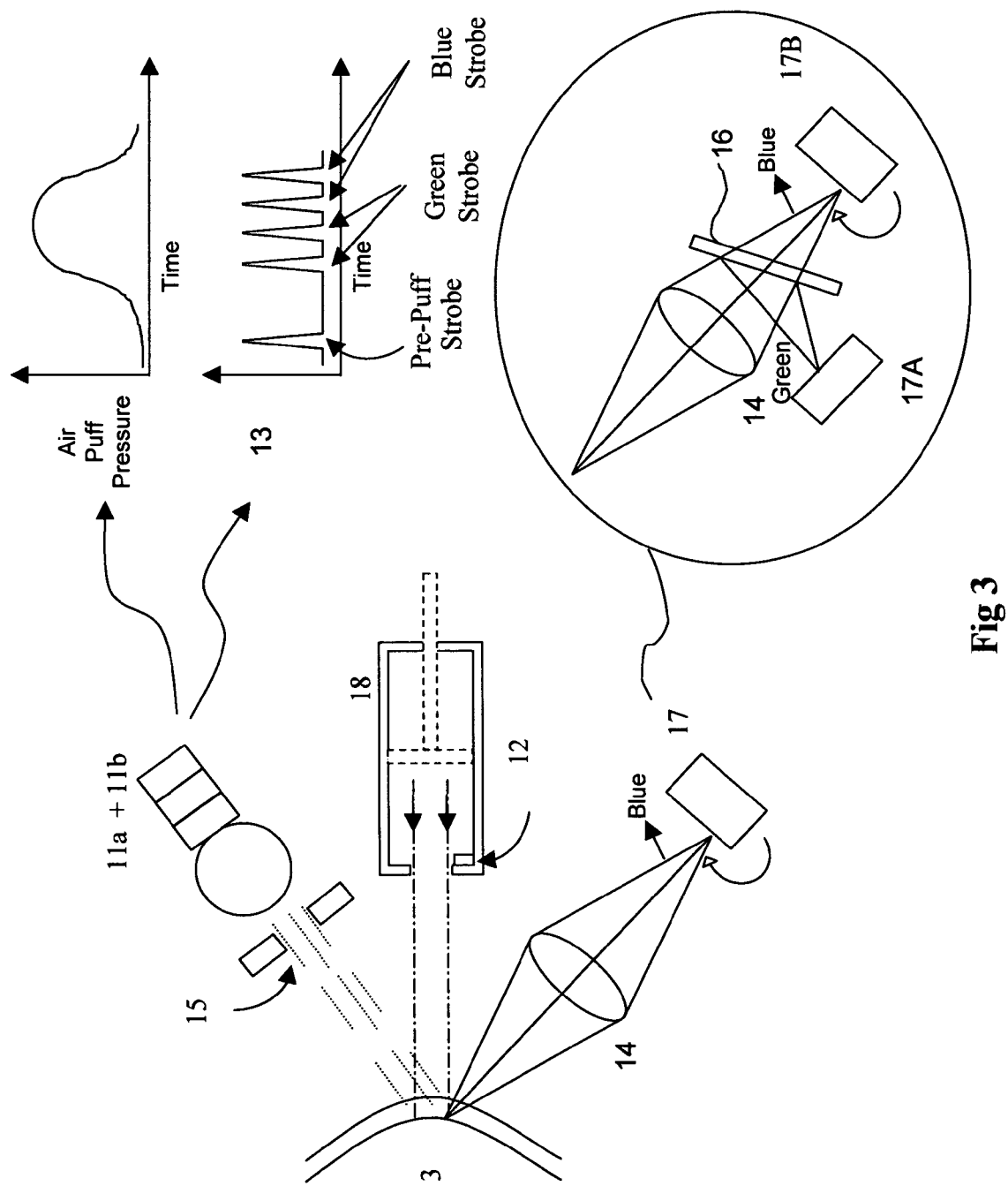
FIG. 3 is a schematic block diagram of a two color strobe light system embodying the present invention of a non-contact corneal biomechanical system.

The above image recording/analysis systems tend be complicated and are intricate to be incorporated physically with the fluid discharging system. 12. Our preferred embodiment, described in FIG. 2 and FIG. 3, is based on the profile photography that are utilizing the scattering and/or reflection of said cornea tissue, 3. FIG. 2 describes the alignment of the system in which the light source, 11*a* and 11*b*, generates a sequence of illuminating light pulses with even intensity through the area of the illuminating beam. Here, a well known Koehler's optical arrangement can reach the objective of the homogeneous illumination. The illuminating light is further conditioned by the adjustable slit, 15, to form an appropriate illuminating profile. Each illumination pulse will have a distinct wavelength as illustrated with blue and green pulse sequence in 12 of FIG. 3. These pulse sequence is generated in this preferred embodiment as illustrated in FIG. 2 and explained below. The pulse width and the duty cycle of the illuminating pulses are determined to distinguish the spatial location of the cornea during the fluid discharge event. The image recording/analysis system comprises of a charge coupled device (CCD) or a complementary metal oxide semiconductor (CMOS), 17. As described in FIG. 1, digital data from this image recording/analysis system will transfer to the microprocessor, 4, or transmitted via the internet, 5, to the server or remote computer, 6, to process the data, 7, and then delivered back to the patient or the physician, 8.

This profile photography can provide information of the cornea thickness, radius of curvature and other topographic characteristics of the cornea as demonstrated in ophthalmic slit lamps and related pachymeters. With this innovation, we will overcome the deficiency of Grabner's proposal and Luce's invention in which either some or all of these cornea parameters are not able to be determined.

To focus the image in the system, this device will be mounted on a positioning system similar to a slit lamp used in ophthalmic offices. The system can be focused to the appropriate location of the patient manually using the alignment optics, 10 of FIG. 2, or through an autofocus system used in a commercially available hand held camera. The autofocusing system is not included in the drawings.

The planes of the CCD or CMOS can be adjustable to meet the Scheimpflug optical requirement. Although this kind of profile photographic system was used in the corneal topographer and pachymeter, for example the U.S. Pat. No. 5,512,966 by Snook and U.S. Pat. No. 6,286,958 by Koest, none of them was incorporated with a fluid discharge system as our dynamic topographer's configuration. The prior inventions are all focused on obtaining the information of cornea thickness and radius of curvature. And none of them was able to provide the biomechanical properties of the cornea.

Although, multiple-frame high speed photography can be used to record images of the whole sequence of the cornea's responses to the fluid discharge, the size of the image data is too big to be cost effective. Our preferred embodiment is described in FIG. 2 and FIG. 3. This preferred embodiment is based on a two-color/detector digital strobe photography of the cornea profiles before and during an air pulse discharging.

The two-color short light pulse sequence, 12 of FIG. 3, is generated by either light emitting diode (LED) or strobe flash lamps. With the LED, the wavelength is determined by the LED used. With strobe flash lamp, wavelength selective color filters will be used with each flash lamp. Strobe pulse sequence, from light source 11*a*, with the first wavelength will be illuminating the cornea concaving process and the other pulse sequence with second wavelength, from light source 11*b*, will illuminate the bouncing back of the cornea in the deformation event. The images of said cornea deformation is thus recorded on CCD/CMOS 17. The difference of the color will determine which images are captured during the flattening and concaving process of the cornea and which images are captured during the bouncing back of the cornea. Another configuration is designed to unequivocally resolve the sequence of the cornea deformation, 12, by using a dichroic filter, 16. The dichroic filter, 16, will reflect first wavelength to one CCD/CMOS, 17*a*, and allow the other color to the other CCD/CMOS, 17*b*. Both 17*a* and 17*b* are housed in part 17. This scheme will prevent the overlap and obscure of the images due to flattening and bouncing back events. In FIG. 3, the first sequence of light pulses are green and the second sequence of light pulses are blue. This is used to demonstrate the concept and not intended to limit our choice of color selection of the light pulses.

Multiple color and multiple dichroic prisms, more than two, can be used to achieve the same goal for more than two wavelengths of strobing light sequences.

In FIG. 3, we use an air plunger, 18, to compress the air through the orifice of an air compartment. Solenoid's or linear motor's, below the optical plane of FIG. 2, are part of the group of devices that can drive the air plunger, 18. The driving force can be modulated to achieve a desirable air pulse profile. The air pulse profile can be monitored by a pressure sensor, 13. This sensor, 13, can be located inside the air compartment or outside of the air compartment. The pressure and temporal profile of the fluid discharge will be used as the stress parameter that will determine the biomechanical properties of the cornea.

Figure 4:
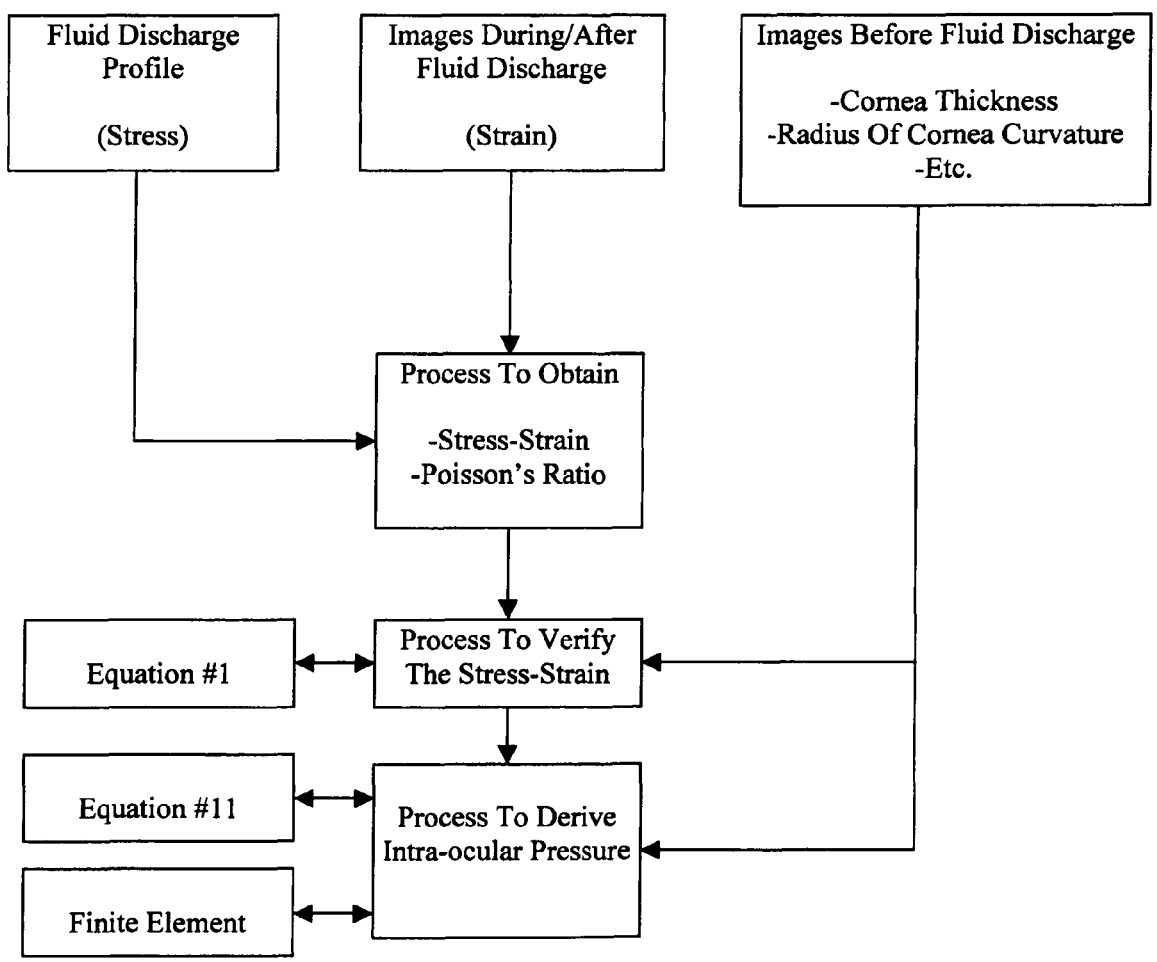
FIG. 4 is a flow chart illustrating the basic protocol to derive the cornea biomechanical properties and intraocular pressure in accordance with the current invention.

FIG. 4 is a schematic flowchart illustrating the sequence of operations used to derive the biomechanics properties and the intraocular pressure in accordance with the embodiment of the present invention. The images recorded will give the locations of the cornea at different times. The sharpness of the image depends on the pulse width of the strobe light and the focusing condition of the image. In our preferred embodiment, the air pulse is about 10 msec, and the strobe light pulse width will be arranged in the range of 10 to 100 μsec. About 20 strobe pulses will be used during the whole event. With the time dependent location of the cornea, we will be able to derive the velocity, acceleration and thus the strain of the cornea due to the stress of the fluid discharge. Before the discharge of the air pulse, a short pulse of light can be initiated to record the cornea profile that produces the information of cornea thickness, radius of curvature and any abnormality of the cornea. This was not included in FIG. 4 to simplify the flow chart.

Knowing the temporal profile of the air pulse and the reaction of the cornea, we can derive the stress-strain relationship of the cornea. Since we are able to measure the whole event of the interaction, we will obtain the stress-strain relationship of the whole effect. If the cornea is elastic, the stress-strain will show a linear pattern and the slope of the stress-strain relationship is the elasticity of the cornea. With elasticity values of the fluid discharge plane and the plane perpendicular to the central axis of the fluid discharge, we can derive the Poisson's ratio. If the cornea is viscoelastic with hysteretic stress-strain relationship, a complex form of elasticity and Poisson's ratio will be derived.

As an alternative to the traditional stress analysis using dimensional domain method, Fourier Transform method can also be used to analyze the stress and strain data. Fourier transform is a mathematical operation that will transform the time dependent data to frequency domain, thus eliminating the instrument and process noise to statistically reveal the response and the linearity relationship between the stress and strain. This method was demonstrated by Wang's in vitro tissue tests.

With the biomechanical properties of the cornea, we can derive the intraocular pressure of the eye via analytical formulae or numerical calculation. Young shows the cornea displacement ($\delta$) of the applanation force is related to the true intraocular pressure (IOPT) as:

$$\delta = (aW(R-t/2)(1-v^2)^{0.5})/Et^2 - (IOPT((R-t/2)(1-v^2))/2Et \quad \text{Equation \#1}$$

Where a is the corneal geometric constant

W is the force generated by the fluid discharge

R is the radius of curvature of the anterior cornea t is the center thickness of the cornea E is the elasticity of the cornea v is the Poisson ration of the cornea Utilizing this simplified equation, Orseenger and Pye could derive an empirical formula for a Goldmann tonometer.

Besides the simplified analytical equation, finite element analysis can also be used to obtain the true intraocular pressure. Once the preliminary data was verified via the analytical formula, we will use the parameters and stress-strain relationship derived from the experiments in the finite element model. Recently, Anderson used the dynamic finite element analysis to evaluate the interaction between a 10 msec air pulse and the cornea. We can use the same dynamic finite element model and adjust the IOP in the calculation until the simulated cornea deformation agrees with the recorded data.

What is claimed:

1. A medical device that is to measure the biomechanical and physical properties of a mammal cornea comprising:
   (A) fluid discharge means of predetermined force that can impact on and deform said cornea in a predetermined area;
   (B) illumination means to project predetermined at least one slit shape of light to illuminate at least a section of said cornea;
   (C) recording means to record at least two dimensional coordinates of said cornea deformed by said fluid discharge; and
   (D) analyzing and calculation means to derive and verify biomechanical properties of said cornea.

2. A device according to claim 1, wherein said means of recording means comprises an arrangement of the planes of an image detector, an image forming optics and said cornea section target to be in compliance with Scheimpflug requirement.

3. A device according to claim 1, wherein said recording means comprises a group of charge coupled devices and complementary metal oxide semiconductors.

4. A device according to claim 1, wherein said illumination means is a sequence of light pulses; said sequence of the light pulses is generated from a device selected from the group comprised of flash lamps, light emitting devices, electro-mechanical modulated shutters and lasers.

5. A device according to claim 1, wherein said illumination means is a sequence of light pulses; said sequence of light pulses comprises at least one pulse of light to illuminates said cornea when said cornea is concaved to the posterior part of said eye as the initial response to said fluid discharge impact approximately during the first half of fluid discharge duration.

6. A device according to claim 1, wherein said illumination means is a sequence of light pulses; said sequence of light pulses comprises at least one pulse of light to illuminates said cornea when it is bounced back from the posterior part of said eye approximately during and immediately after the second half of fluid discharge duration.

7. A device according to claim 1, wherein said illumination means is a sequence of light pulses; said sequence of light pulses comprises at least one pulse of light has a pulse width that is a fraction of the pulse width of said fluid discharge so the topographic deformation event of said cornea can be resolved on said recording means.

8. A device according to claim 1, wherein said illumination means is a sequence of light pulses comprises at least two different wavelengths; light pulses with one wavelength illuminate said cornea when said cornea is concaved to the posterior part of the eye as the initial response to said fluid discharge impact; light pulses with the other wavelengths are used to illuminate said cornea when it is rebound back to the normal position in the second half of said fluid discharge duration and immediately after said fluid discharge impact; and both concaving and rebounding events are thus recorded on the recording means.

9. A device according to claim 1, wherein recording means comprises a color recording means that can record at least two colors of said topographic deformation history that are generated by said illumination means comprising at least two wavelengths.

10. A device according to claim 1, wherein recording means with a component selected from a group of a high speed video or high speed multiple-frame photographic imaging systems to record cornea deformation event of at least the anterior surface of said eye.

11. A device according to claim 1, wherein said fluid discharge is an air pulse.

12. The fluid discharge according to claim 11, wherein said air pulse is generated by compressing atmospheric air in a compartment through an output orifice.

13. The fluid discharge according to claim 11, wherein said air pulse is generated by releasing compressed air in an enclosed compartment via a switch.

14. A device according to claim 1, wherein the pressure profile of said fluid discharge is monitored during said fluid discharge with a component selected from a group of piezo-electric and opto-mechanical sensors whereby said pressure profile will be used to derive the stress-strain relationship of said cornea and the biomechanical properties of said cornea.

15. A medical device that is to measure the biomechanical and physical properties of a mammal cornea comprising:
   (A) illumination means to project at least one slit shape of light to illuminate a section of said cornea and recording means to record at least two dimensional coordinates of said cornea to derive the physical dimension of said cornea comprising at least a radius of curvature of said cornea, a thickness of said cornea and other abnormity of said cornea prior to a fluid discharge;
   (B) fluid discharging means of predetermined force that impact on and deform said cornea in a predetermined area;

(C) illumination means and recording means same as in (A) to record at least two dimensional coordinates of said cornea section deformed by the said fluid discharge;

(D) recording means to record at least two dimensional coordinates of said section of cornea deformed by said fluid discharge; and (E) means to derive the biomechanical properties of said cornea; whereby the sequence of the topographic changes will produce the strain profile of said cornea; the pressure profile of said fluid discharge is the stress;

(F) means to verify the biomechanical properties of said eye with mechanical methods selected from the group of analytical and numerical mechanical methods comprises of finite difference or finite element.

16. A device according to claim 15, wherein means to derive the stress-strain relationship of said cornea comprises of physical dimension domain and time domain means applied to the topographic changes of said cornea and said impact fluid discharge.

17. A device according to claim 15, wherein said means of recording the cornea deformation comprises an arrangement of the planes of an image detector, an image forming optics and said cornea target to be in compliance with Scheimpflug requirement.

18. A device according to claim 15, wherein illumination and recording means comprises of a plurality of orientations in space so multiple profiles with plurality of physical dimensions can be obtained in the cases of corneas with unsymmetrical topography including astigmatism.

19. A device according to claim 15, wherein means of deriving and verifying the stress-strain relationship can be carried out in the vicinity of the measurement system.

20. A device according to claim 15, wherein means of deriving and verifying the stress-strain relationship can be carried out in centers with computation capability via internet.

21. A device according to claim 15, wherein said recording means comprises a group of charge coupled devices and complementary metal oxide semiconductors.

22. A device according to claim 15, wherein said illumination means is a sequence of light pulses; said sequence of the light pulses is generated from a device selected from the group comprised of flash lamps, light emitting devices, electro-mechanical modulated shutters and lasers.

23. A device according to claim 15, wherein said illumination means is a sequence of light pulses; said sequence of light pulses comprises at least one pulse of light to illuminates said cornea when said cornea is concaved to the posterior part of said eye as the initial response to said fluid discharge impact approximately during the first half of fluid discharge duration.

24. A device according to claim 15, wherein said illumination means is a sequence of light pulses; said sequence of light pulses comprises at least one pulse of light to illuminates said cornea when it is bounced back from the posterior part of said eye approximately during and immediately after the second half of fluid discharge duration.

25. A device according to claim 15, wherein said illumination means is a sequence of light pulses; said sequence of light pulses comprises at least one pulse of light which has a pulse width that is a fraction of the pulse width of said fluid discharge so the topographic deformation event of said cornea can be resolved on said recording means.

26. A device according to claim 15, wherein said illumination means is a sequence of light pulses comprises at least two different wavelengths; light pulses with one wavelength illuminate said cornea when said cornea is concaved to the posterior part of the eye as the initial response to said fluid discharge impact; light pulses with the other wavelengths are used to illuminate said cornea when it is rebound back to the normal position in the second half of said fluid discharge and immediately after said fluid discharge impact; both concaving and rebounding events are thus recorded by the recording means.

27. A device according to claim 15, wherein said recording means comprises a color recording component that can record at least two colors of said topographic deformation events of said cornea that are illuminated by said illumination means comprising at least two wavelengths of light.

28. A device according to claim 15, wherein said recording means comprises a plurality of the black and white image recording components that can record deformation events immediately after a group of dichroic prisms or filters to differentiate the event images illuminated by said illumination means comprising at least two wavelengths of light.

29. A device according to claim 15, wherein said fluid discharge is an air pulse.

30. The fluid discharge according to claim 29, wherein said air pulse is generated by compressing atmospheric air in a compartment through an output orifice.

31. The fluid discharge according to claim 29, wherein said air pulse is generated by releasing compressed air in an enclosed compartment via a switch.

32. A device according to claim 15, wherein the pressure profile of said fluid discharge is monitored during said fluid discharge with a device selected from a group of piezoelectric and opto-mechanical sensors whereby said pressure profile will be used to derive the stress-strain relationship of the cornea and the biomechanical properties of the cornea.

33. A device according to claim 15, wherein said means to derive the biomechanical properties of said cornea is selected from a group of analytical and numerical mechanical methods comprising of finite difference, finite element modeling and analytical formula.

34. A device according to claim 15, wherein said means to verify the biomechanical properties of said cornea comprises of using eye model and statistical evaluation of clinical data.

* * * * *